(12) United States Patent
Tsuchiya et al.

(10) Patent No.: US 7,301,626 B2
(45) Date of Patent: Nov. 27, 2007

(54) LASER-SCANNING EXAMINATION APPARATUS

(75) Inventors: Atsuhiro Tsuchiya, Hachioji (JP); Yoshihiro Kawano, Hachioji (JP); Yoshihisa Tanikawa, Chuo-ku (JP); Tadashi Hirata, Hachioji (JP)

(73) Assignee: Olympus Corporation, Tokyo (JP)

( * ) Notice: Subject to any disclaimer, the term of this patent is extended or adjusted under 35 U.S.C. 154(b) by 121 days.

(21) Appl. No.: 11/182,782

(22) Filed: Jul. 18, 2005

(65) Prior Publication Data

US 2006/0017920 A1    Jan. 26, 2006

(30) Foreign Application Priority Data

Jul. 26, 2004    (JP) ............................ 2004-217605

(51) Int. Cl.
*G01J 3/30*    (2006.01)
(52) U.S. Cl. ............... 356/317; 250/453.11; 250/461.2
(58) Field of Classification Search ............... 356/625, 356/432, 317; 385/31, 43, 7, 88; 359/385; 250/453.11, 461.2; 600/245, 246
See application file for complete search history.

(56) References Cited

U.S. PATENT DOCUMENTS 6,269,206 B1 * 7/2001 Simon et al. ................. 385/31

2002/0045890 A1 * 4/2002 Celliers et al. ................. 606/7
2005/0271336 A1 * 12/2005 Galstian et al. ............... 385/95

FOREIGN PATENT DOCUMENTS

JP    2002-243641    8/2002

* cited by examiner

*Primary Examiner*—Gregory J. Toatley
*Assistant Examiner*—Abdullahi Nur
(74) *Attorney, Agent, or Firm*—Kenyon & Kenyon LLP

(57) ABSTRACT

The invention reduces the loss of fluorescence intensity obtained from a specimen to acquire clear fluorescence images when irradiating the specimen with ultrashort-pulse laser light produced by a laser light source. The invention provides a laser-scanning examination apparatus including a laser light source for producing ultrashort-pulse laser light; a laser light source for producing continuous-wave laser light; a measurement head including an optical scanning unit for scanning the laser light on a specimen and an objective optical system; an imaging unit for detecting return light from the specimen in response to the ultrashort-pulse laser light; and an imaging unit for detecting return light from the specimen in response to the continuous-wave laser light. The laser light sources and one imaging unit are connected to the measurement head by an optical fiber, and the other imaging unit is connected to the measurement head by another optical fiber with a larger core diameter.

9 Claims, 9 Drawing Sheets

FIG. 3
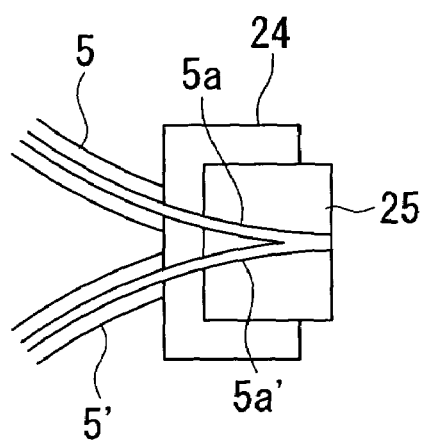
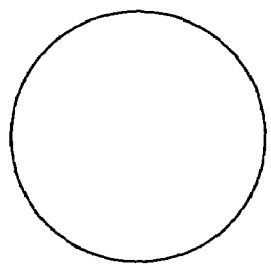
FIG. 5A
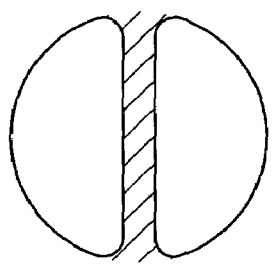
FIG. 5B
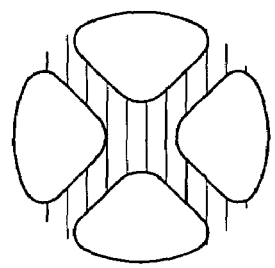
FIG. 5C

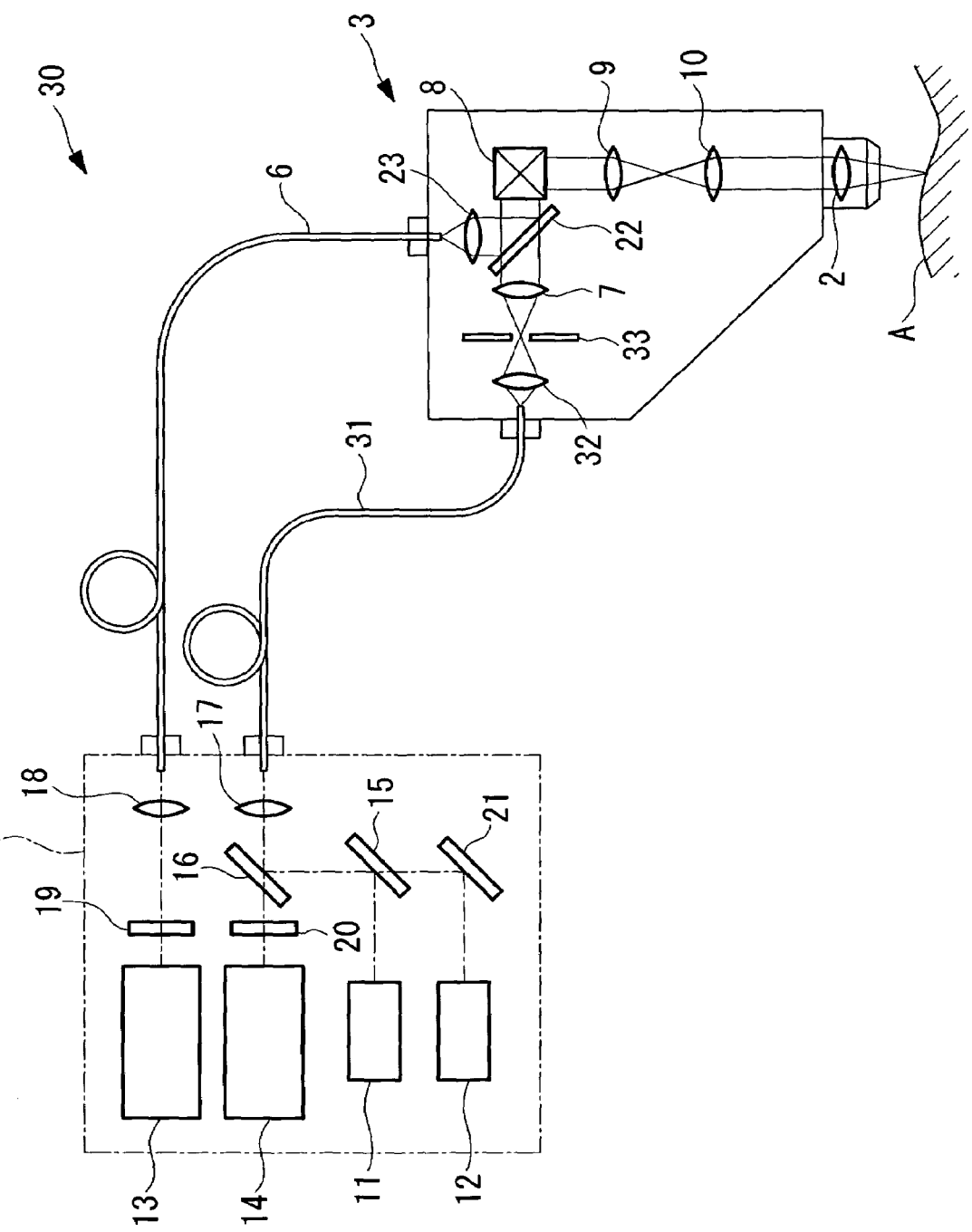

LASER-SCANNING EXAMINATION APPARATUS

BACKGROUND OF THE INVENTION

1. Field of the Invention

The present invention relates to a laser-scanning examination apparatus.

This application is based on Japanese Patent Application No. 2004-217605, the content of which is incorporated herein by reference.

2. Description of Related Art

Known apparatuses in the related art for observing cellular function and the like by irradiating a specimen, such as a living organism, from the surface thereof with excitation light and detecting fluorescence generated at a comparatively deep position below the surface of the specimen include multiphoton-excitation-type examination apparatuses (see, for example, Japanese Unexamined Patent Application Publication No. 2002-243641, page 3, etc.).

This multiphoton-excitation-type examination apparatus has a configuration in which fluorescence emitted from the specimen is detected by an external photomultiplier tube that is connected via a single-mode fiber.

However, the single-mode fiber suffers from the drawback that it is not possible to carry out measurement efficiently because the core diameter is narrow and thus fluorescence returning from the specimen is spatially confined. In order to more efficiently measure the fluorescence, it is preferable to dispose the photomultiplier tube directly after the objective lens in the measurement head; in such a case, however, since the photomultiplier tube is comparatively large, the measurement head itself becomes larger and therefore is not suitable for use in applications where it needs to be disposed at various orientations and positions according to the examination site in the specimen, for example, when carrying out in-vivo examination of small laboratory animals.

On the other hand, a multimode fiber has been considered for use as an optical fiber that has a large core diameter and thus does not confine the fluorescence from the specimen; however, light of multiple transmission modes propagates in multimode fibers. As a result, when ultrashort-pulse laser light from a laser light source is introduced thereto, multiple mode splitting occurs, which increases the pulse width. Such light has a drawback in that it is not possible to efficiently generate the multiphoton-excitation effect.

BRIEF SUMMARY OF THE INVENTION

The present invention has been conceived in light of the situation described above, and an object thereof is to provide laser-scanning examination apparatus that can reduce the loss of fluorescence intensity obtained from a specimen, while irradiating the specimen with ultrashort-pulse laser light produced by a laser light source, thus enabling the acquisition of bright fluorescence images and that can make the configuration of the measurement head more compact.

In order to achieve the object described above, the present invention provides the following solutions.

According to a first aspect, the present invention provides a laser-scanning examination apparatus including a first laser light source for producing ultrashort-pulse laser light; a second laser light source for producing continuous-wave laser light; a measurement head including an optical scanning unit for scanning the laser light from the laser light sources on a specimen and an objective optical system for imaging the laser light scanned by the optical scanning unit onto the specimen; a first imaging unit for detecting return light from the specimen in response to the ultrashort-pulse laser light from the first laser light source; a second imaging unit for detecting return light from the specimen in response to the continuous-wave laser light from the second laser light source; a first optical fiber for connecting the first laser light source, the second laser light source, and the second imaging unit with the measurement head; and a second optical fiber, having a core diameter larger than the first optical fiber, for connecting the first imaging unit with the measurement head.

According to this aspect, the ultrashort-pulse laser light produced by the first laser light source is transmitted by the first optical fiber, enters the measurement head, is scanned by the operation of the optical scanning unit, and is imaged onto the specimen by the objective optical system. Return light produced in the specimen by irradiating it with the ultrashort-pulse laser light returns via the objective optical system and the optical scanning unit, passes through the second optical fiber, and is detected by the first imaging unit.

In such a case, since the second optical fiber has a core diameter larger than the first optical fiber, the ultrashort-pulse laser light introduced to the measurement head does not experience multiple mode splitting in the first optical fiber, and furthermore, the return light from the specimen can be efficiently transmitted by the second optical fiber to reach the first imaging unit.

Connecting the measurement head, the light sources, and the imaging units with optical fibers allows the measurement head to be kept small, and in addition, the measurement head can be freely disposed at any orientation and position by manipulating the optical fibers.

In the aspect of the invention described above, the first optical fiber may be disposed at the center of the second optical fiber. By doing so, it is possible to simplify the configuration using a single optical fiber, thus allowing the degree of freedom of manipulation to be further improved.

The aspect of the invention described above may also include a light-path switching mechanism, and the first imaging unit and the second imaging unit may be constituted of the same imaging unit. In this case, the light-path switching mechanism switches between a light path linking the first optical fiber and the imaging unit and a light path linking the second optical fiber and the imaging unit.

By switching between the return light returning from the measurement head via the first optical fiber and return light returning via the second optical fiber with the operation of the light-path switching mechanism, it is possible to use a single common imaging unit, which allows the configuration to be simplified and the apparatus made more compact.

According to a second aspect, the present invention provides a laser-scanning examination apparatus including a first laser light source for producing ultrashort-pulse laser light; a second laser light source for producing continuous-wave laser light; a measurement head including an optical scanning unit for scanning the laser light from the laser light sources on a specimen and an objective optical system for imaging laser light scanned by the optical scanning unit onto the specimen; a first imaging unit for detecting return light from the specimen in response to the ultrashort-pulse laser light from the first laser light source; a second imaging unit for detecting return light from the specimen in response to the continuous-wave laser light from the second laser light source; a first optical fiber for connecting the first laser light source and the first imaging unit with the measurement head; a second optical fiber for connecting the second laser light source with the measurement head; and a third optical fiber, having a core diameter larger than the first and second optical fibers, for connecting the second imaging unit with the measurement head.

According to this aspect, since the third optical fiber has a larger core diameter than the first and second optical fibers, the ultrashort-pulse laser light introduced to the measurement head experiences no multiple mode splitting in the first optical fiber, and furthermore, return light from the specimen can be efficiently transmitted by the third optical fiber to reach the first imaging unit.

Connecting the measurement head, the light sources, and the imaging units with optical fibers prevents the measurement head from becoming larger, and in addition, the measurement head can be freely disposed at any orientation and position by manipulating the optical fibers.

In the aspect of the invention described above, the first optical fiber and the second optical fiber are preferably formed of single-mode fibers or photonic crystal fibers, and a cutoff wavelength of the second optical fiber is preferably set to be smaller than a cutoff wavelength of the first optical fiber.

With such a configuration, it is possible to use a single-mode fiber or a photonic crystal fiber having a cutoff wavelength that matches the wavelength of the transmitted light.

According to a third aspect, the present invention provides a laser-scanning examination apparatus including a first laser light source for producing ultrashort-pulse laser light; a second laser light source for producing continuous-wave laser light; a measurement head including an optical scanning unit for scanning the laser light from the laser light sources on a specimen and an objective optical system for imaging the laser light scanned by the optical scanning unit onto the specimen; a first imaging unit for detecting return light from the specimen in response to the ultrashort-pulse laser light from the first laser light source; a second imaging unit for detecting return light from the specimen in response to the continuous-wave laser light from the second laser light source; a multimode fiber for connecting the first laser light source, the second laser light source, and the first imaging unit with the measurement head; one of a multimode fiber and a fiber bundle for connecting the second imaging unit and the measurement head. The measurement head includes a focusing lens that forms an intermediate image of the laser light from the coming from first and second laser light sources and transmitted by the multimode fiber, and a pinhole member, disposed close to the position of the intermediate image, that admits passage of only the vicinity of the center of the intermediate image.

According to this aspect, the ultrashort-pulse laser light emitted from the first laser light source is introduced into the measurement head via the multimode fiber, and after being focused by the focusing lens, passes through the pinhole member in the vicinity of the intermediate image position. The pinhole member admits passage of only light near the center of the intermediate image, that is to say, only light propagating near the center of the multimode fiber.

Because only the ultrashort-pulse laser light of the lowest-order mode propagates near the center of the multimode fiber, only the ultrashort-pulse laser light of the lowest-order mode is allowed to pass by the pinhole member. As a result, the light of the lowest-order mode does not experience multiple mode splitting in the multimode fiber, and it is thus possible to emit light that is comparatively phase coherent from the objective optical system towards the specimen. As a result, it is possible to efficiently produce the multiphoton-excitation effect in the specimen.

The return light from the specimen is introduced to the first imaging unit via the multimode fiber. Since the multimode fiber has a large core diameter, the return light reaches the first imaging unit without being spatially confined, and the return light can thus be efficiently detected.

In the aspect of the invention described above, the diameter of an opening in the pinhole member may be variable. By doing so, the confocal effect (resolution in the optical-axis direction) can be adjusted. It is therefore possible to increase the confocal effect to allow acquisition of clear images, and to ensure return light of sufficient intensity to acquire bright images, instead of reducing the confocal effect.

According to a fourth aspect, the present invention provides a laser-scanning examination apparatus including a first laser light source for producing ultrashort-pulse laser light; a second laser light source for producing continuous-wave laser light; a measurement head including an optical scanning unit for scanning the laser light from the laser light sources on a specimen and an objective optical system for imaging the laser light scanned by the optical scanning unit onto the specimen; an imaging unit for detecting return light from the specimen in response to the laser light from the first and second laser light sources; and a multimode fiber for connecting the first laser light source, the second laser light source, and the imaging unit with the measurement head. The measurement head includes a focusing lens that forms an intermediate image of the laser light coming from the first and second laser light sources and transmitted by the multimode fiber, and a pinhole member, provided in near the position of the intermediate image, that admits passage of only the vicinity of the center of the intermediate image, and the pinhole member is formed of a material that blocks the ultrashort-pulse laser light, the continuous-wave laser light, and return light from the specimen in response to the continuous-wave laser light and that allows passage of the return light from the specimen in response to the ultrashort-pulse laser light.

According to this embodiment, in the ultrashort-pulse laser light from the first laser light source, only the ultrashort-pulse laser light of the lowest-order mode at the center of the multimode fiber is allowed to pass by the pinhole member, which allows the multiphoton-excitation effect to be efficiently produced in the specimen. On the other hand, the return light returning from the specimen is efficiently introduced into the multimode fiber without reducing the light intensity due to the pinhole effect produced by the pinhole member, which allows bright, detailed images to be acquired. Also, the continuous-wave laser light from the second laser light source experiences the pinhole effect due to the pinhole member, which allows detailed images to be acquired. In this case, the two laser light sources and the measurement head can be connected by a single multimode fiber, which allows the measurement head to be more easily manipulated.

The present invention provides an advantage in that it can reduce the amount of loss of the fluorescence obtained from a specimen when irradiating the specimen with ultrashort-pulse laser light emitted by a laser light source, which allows bright fluorescence images to be acquired, and in addition, the measurement head configuration can be made compact.

BRIEF DESCRIPTION OF THE SEVERAL VIEWS OF THE DRAWINGS

FIG. 3 is a longitudinal sectional view showing an example of the structure at a light-emitting end of an optical fiber in the laser-scanning examination apparatus in FIG. 2.

FIG. 4 is a schematic diagram showing the overall configuration of a laser-scanning examination apparatus according to a second embodiment of the present invention.

FIGS. 5A to 5C are schematic diagrams for explaining transmission modes of ultrashort-pulse laser light in the optical fiber of the laser-scanning examination apparatus in FIG. 4.

DETAILED DESCRIPTION OF THE INVENTION

A laser-scanning examination apparatus according to an embodiment of the present invention will be described below with reference to FIG. 1.

Figure 1:
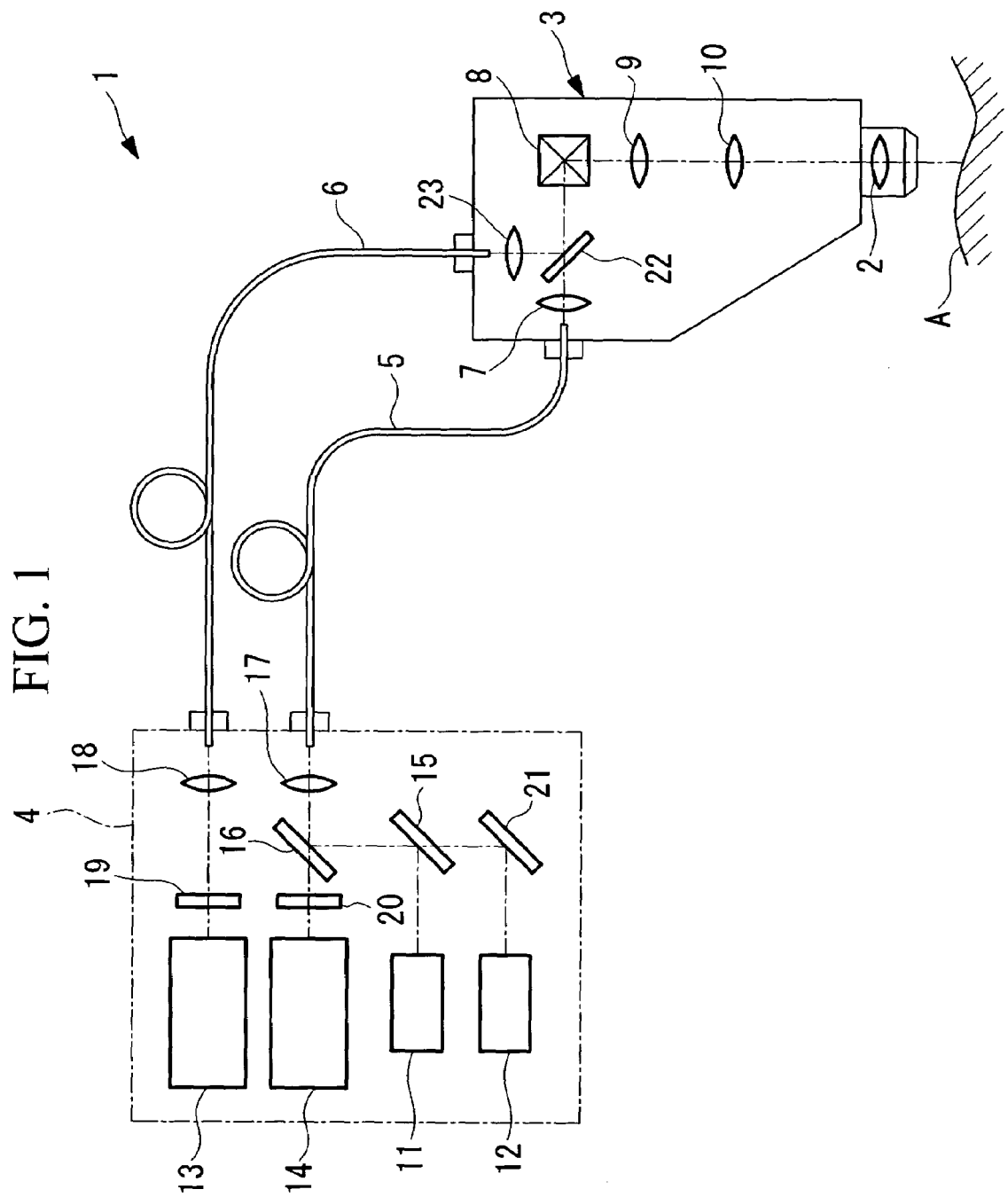
FIG. 1 is a schematic diagram showing the overall configuration of a laser-scanning examination apparatus according to a first embodiment of the present invention.

As shown in FIG. 1, a laser-scanning examination apparatus 1 according to this embodiment includes a measurement head 3 having an objective lens 2 that is positioned opposite a specimen A, such as a small laboratory animal, an optical unit 4, and optical fibers 5 and 6 that connect the measurement head 3 and the optical unit 4.

The measurement head 3 includes a collimator lens 7, a laser-scanning unit 8, a pupil-projection lens 9, and an imaging lens 10. The collimator lens 7 converts the laser beam transmitted by the optical fiber 5 into a collimated beam. The laser scanning unit 8 includes, for example, two galvano mirrors (not shown in the drawing) that can be rotated about two mutually orthogonal axes and varies the deflection angle of the laser beam so as to two-dimensionally scan the beam on the specimen A. The pupil-projection lens 9 images the laser beam that is two-dimensionally scanned by the laser-scanning unit 8 to form an intermediate image. The imaging lens 10 collects the laser light forming the intermediate image so that the light is made incident on the objective lens 2.

Although not shown in the figure, the measurement head 3 is supported by an arm so as to be freely movable.

The optical unit 4 includes a first laser light source 11 that generates near-infrared ultrashort-pulse laser light having, for example, a pulse width of about 100 fs (femtoseconds) and a wavelength of about 976 nm; a second laser light source 12 that generates continuous-wave (cw) laser light having a wavelength of about 488 nm; a first optical detector 13 for fluoroscopy using the near-infrared ultrashort-pulse laser light from the first laser light source 11; and a second optical detector 14 for fluoroscopy using the continuous-wave laser light from the second laser light source 12.

The optical axes of the first laser light source 11 and the second laser light source 12 are combined by a dichroic mirror 15. The optical axis of the second optical detector 14 is combined with the combined optical axis of these two laser light sources 11 and 12 by a dichroic mirror 16.

The combined optical axis of the two laser light sources 11 and 12 and the second optical detector 14 is aligned with one end of the first optical fiber 5 via a coupling lens 17. As well as focusing the laser beams from the laser light sources 11 and 12 onto the end of the optical fiber 5, the coupling lens 17 simultaneously collects fluorescence from the first optical fiber 5 and guides it to the second optical detector 14. The optical axis of the first optical detector 13 is aligned with one end of the second optical fiber 6 via a collimator lens 18. The collimator lens 18 also collects fluorescence from the second optical fiber 6 and guides it to the first optical detector 13.

The first optical detector 13 and the second optical detector 14 are photomultiplier tubes, for example. Barrier filters 19 and 20 that admit only fluorescence with wavelengths to be detected by the respective optical detectors 13 and 14 to pass therethrough are disposed in front of the optical detectors 13 and 14. Reference numeral 21 represents a mirror.

The other ends of the first optical fiber 5 and the second optical fiber 6 are connected to the measurement head 3. A dichroic mirror 22 is disposed between the collimator lens 7 and the laser scanning unit 8 in the measurement head 3, for splitting return light returning from the laser scanning unit 8 to the other end of the first optical fiber 5 and to the other end of the second optical fiber 6.

The collimator lens 7 serves as a coupling lens for coupling light into the other end of the first optical fiber 5, and a coupling lens 23 for focusing the light split off by the dichroic mirror 22 onto the other end of the second optical fiber 6 is provided between the dichroic mirror 22 and the other end of the second optical fiber 6.

In this embodiment, the first optical fiber 5 is a single-mode fiber having a core diameter of several microns or a photonic crystal fiber. The second optical fiber 6 is a multi-mode fiber having a core diameter of several millimeters or a fiber bundle.

The operation of the laser-scanning examination apparatus 1 according to this embodiment, having such a configuration, will be described below.

The laser-scanning examination apparatus 1 according to this embodiment selectively switches between the first laser light source 11 and the second laser light source 12.

The near-infrared ultrashort-pulsed laser beam emitted by the first laser light source 11 and the continuous-wave laser beam emitted from the second laser light source 12 pass through the dichroic mirrors 15 and 16 and are made incident on the first optical fiber 5 by the coupling lens 17. Then, the beams are transmitted through the first optical fiber 5 and enter the measurement head 3, where they are converted to collimated beams by the collimator lens 7.

The collimated near-infrared ultrashort-pulsed laser beam is two-dimensionally scanned by the operation of the laser scanning unit 8, passes through the pupil-projection lens 9, the imaging lens 10, and the objective lens 2, and is irradiated onto the specimen A. As a result of the multiphoton-excitation effect, fluorescence is generated in the specimen A at a predetermined position in the depth direction where the near-infrared ultrashort-pulsed laser beam is focused. Then, the fluorescence produced returns along the same path via the objective lens 2, the imaging lens 10, the pupil-projection lens 9, and the laser scanning unit 8, and is split off from the light path by the dichroic mirror 22.

The fluorescence that is split off is focused onto the end face of the second optical fiber 6 by the coupling lens 23, is transmitted through the second optical fiber 6, and returns to the optical unit 4. Then, after being collimated by the collimator lens 18, light of unwanted wavelengths is removed by the barrier filter 19 and the remainder is detected by the optical detector 13.

On the other hand, the continuous-wave laser beam emitted by the second laser light source 12 is two-dimensionally scanned by the operation of the laser scanning unit 8, passes through the pupil-projection lens 9, the imaging lens 10, and the objective lens 2, and is irradiated onto the specimen A. Fluorescence is produced in the specimen A at each position in the depth direction where it is irradiated by the continuous-wave laser beam. Then, the fluorescence produced returns to the optical unit 4 via the objective lens 2, the imaging lens 10, the pupil-projection lens 9, the laser scanning unit 8, the dichroic mirror 22, the collimator lens 7, and the first optical fiber 5, passes through the coupling lens 17, the dichroic mirror 16, and the barrier filter 20, and is detected by the second optical detector 14.

With such a configuration, the near-infrared ultrashort-pulsed laser beam from the first laser light source 11 is transmitted through the first optical fiber 5 as a single transmission mode to enter the measurement head 3. Therefore, it is possible to prevent lengthening of the pulse width of the ultrashort-pulse laser beam, which occurs in the case of transmission through a multi-mode fiber, which allows the specimen A to be irradiated with ultrashort-pulse laser light having the same short pulse width as that originally emitted by the first laser light source 11. Therefore, it is possible to efficiently generate the multiphoton-excitation effect in the specimen A.

Furthermore, instead of passing through the first optical fiber 5, which has a small core diameter, the fluorescence generated by the multiphoton-excitation effect is split off before reaching the first optical fiber 5 and passes through the second optical fiber 6, which has a large core diameter, to be efficiently detected by the first optical detector 13.

Since the multiphoton excitation has an effect of cutting defocused images, there is no need to return it via the first optical fiber 5, which functions as a confocal pinhole.

The continuous-wave laser beam from the second laser light source 12 is transmitted through the first optical fiber 5 and enters the measurement head 3, and fluorescence produced in the specimen A returns via the first optical fiber 5. However, since the first optical fiber 5 has a core diameter of several microns, the end face of the first optical fiber 5 functions as a confocal pinhole. That is, the end face of the first optical fiber 5 and the position of the image formed at the specimen by the objective lens 2 are in a conjugate positional relationship, and therefore, only the fluorescence produced at the image position of the objective lens 2 can pass through the end face of the first optical fiber 5. As a result, by disposing the image position of the objective lens 2 at a predetermined depth in the specimen A, defocused images can be cut, due to the confocal effect, which allows images of a thin, wide area of tissue below the surface of the specimen to be acquired non-invasively.

In other words, according to the present invention, it is possible to switch between images of a thin, wide region of tissue below the surface of the specimen A obtained by the confocal effect and images of a region of tissue at a deeper position obtained by the multiphoton-excitation effect. In such a case, since the laser beams from the first laser light source 11 for multiphoton excitation and the second laser light source 12 for confocal examination are both transmitted through the same fiber, that is, the first optical fiber 5, the configuration of the system can be reduced in size.

Also, since the fluorescence produced by the multiphoton-excitation effect is transmitted by the second optical fiber 6, which has a larger core diameter, an advantage is provided in that it is possible to acquire the fluorescence efficiently, which improves the degree of precision of the examination. Moreover, since the optical unit 4 and the measurement head 3 are connected by the optical fibers 5 and 6, the optical detectors 13 and 14, whose size is comparatively large, can be separated from the measurement head 3, which allows the measurement head 3 to be made more compact, and also, it is possible to carry out examination from any position and orientation by manipulating the measurement head 3.

Figure 2:
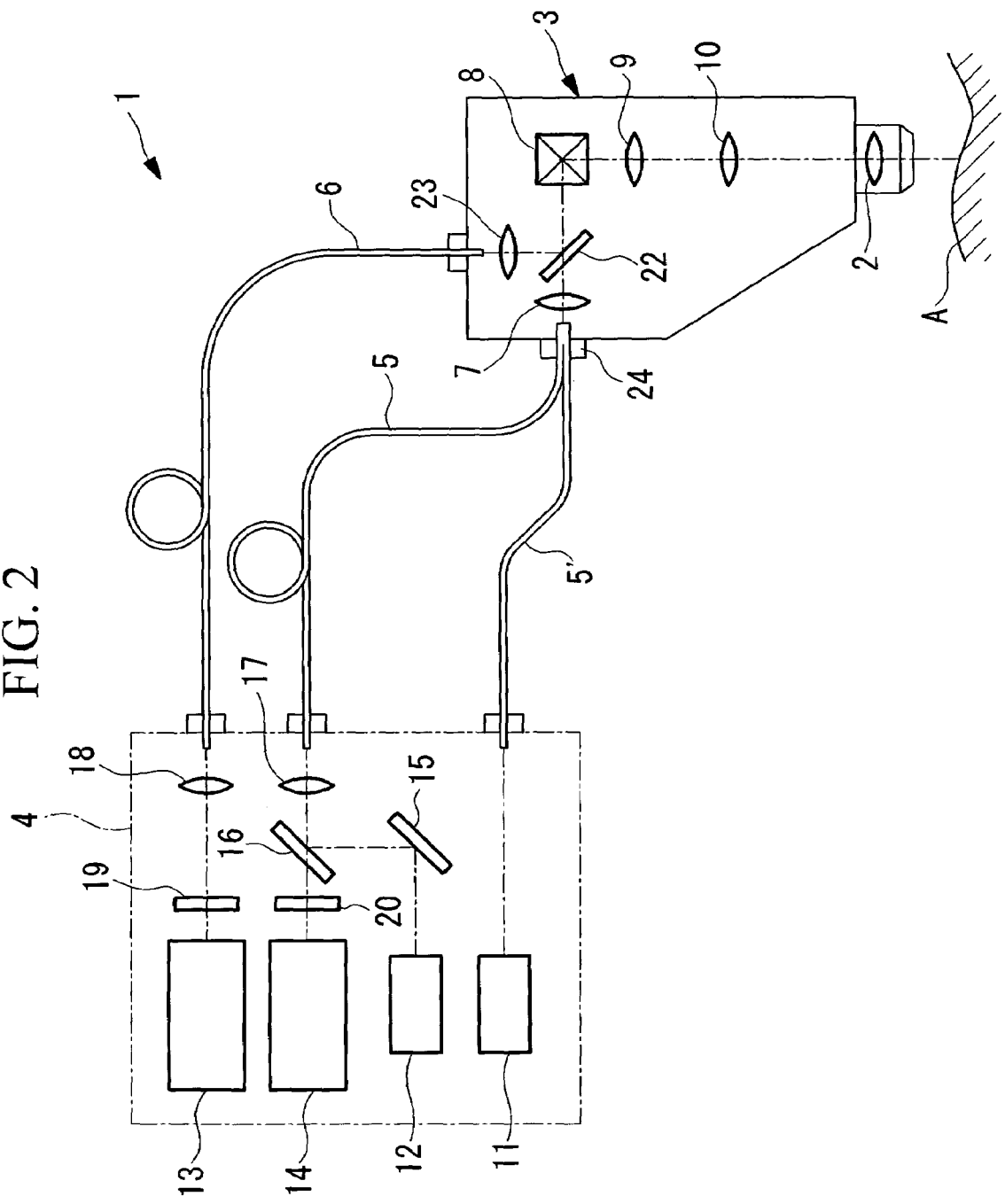
FIG. 2 is a schematic diagram showing a modification of the laser-scanning examination apparatus in FIG. 1.

In the embodiment described above, only a single first optical fiber 5 formed of a single-mode fiber or a photonic crystal fiber is employed as the optical fiber for guiding the laser beams from the first laser light source 11 and the second laser light source 12 to the measurement head 3. Instead of this, however, as shown in FIG. 2, the first laser light source 11 which emits near-infrared ultrashort-pulse laser light may be connected to the measurement head 3 by a first optical fiber 5' that is formed of a single-mode fiber or a photonic crystal fiber, the second laser light source 12 and second optical detector 14 may be connected to the measurement head 3 by a separate second optical fiber 5 formed of a single-mode fiber or a photonic crystal fiber, and the first optical detector 13 and the measurement head 3 may be connected by a third optical fiber 6 formed of a multi-mode fiber or a fiber bundle.

In this case, the first optical fiber 5' and the second optical fiber 5 are preferably supported at a connection part 24 for connecting to the measurement head 3 by a ferrule 25 which is configured so as to join together cores 5a' and 5a at the light-emitting ends of the fibers 5' and 5, respectively, as shown in FIG. 3. By doing so, the light-emitting ends can be disposed on substantially the same optical axis.

In such a case, the cutoff wavelength of the first optical fiber 5' is preferably set to be slightly lower than the wavelength (for example, 488 nm) of the second laser light source 12, for example, at a wavelength of 450 nm, and the cutoff wavelength of the second optical fiber 5 is preferably set to be slightly lower than the wavelength (for example, 976 nm) of the first laser light source 11, for example, at a wavelength of 950 nm. By doing so, it is possible to more reliably maintain the laser light from the light sources 11 and 12 in a single mode for transmission to the measurement head 3, which enables more efficient generation of the multiphoton-excitation effect.

Next, a laser-scanning examination apparatus 30 according to a second embodiment of the present invention will be described below with reference to FIG. 4.

In the description of this embodiment, parts having the same configuration as those in the laser scanning examination apparatus 1 according to the first embodiment shown in FIG. 1 are assigned the same reference numerals and a description thereof shall be omitted.

Whereas the laser-scanning examination apparatus 1 according to the first embodiment uses a single-mode fiber or a photonic crystal fiber as a first optical fiber 5, the laser-scanning examination apparatus 30 according to this embodiment differs in that it uses a first optical fiber 31 formed of a multi-mode fiber. Another difference is that, in the measurement head 3, a focusing lens 32 and a pinhole member 33 are disposed in front of a collimator lens 7 so as to oppose the light-emitting end of the first optical fiber 31.

The pinhole member 33 is disposed in the vicinity of the image formed by the focusing lens 32, and the diameter of the opening thereof is of a size that admits passage of only the central part of an image of the light-emitting end of the first optical fiber 31, which exists at the image position. Also, the pinhole member 33 is disposed at a mutually conjugate position with respect to the image position formed on the specimen A by an objective lens 2.

A dichroic mirror 22, which splits off light returning from the specimen A towards the tip of a second optical fiber 6, is disposed between the collimator lens 7 and a laser scanning unit 8. Therefore, before being incident on the pinhole member 33, fluorescence returning via the laser scanning unit 8 is separated, according to wavelength, into fluorescence that is split off by the dichroic mirror 22 to be incident on the second optical fiber 6 and fluorescence that is transmitted through the dichroic mirror 22, passes through the collimator lens 7, the pinhole member 33, and the focusing lens 32 to be incident on the first optical fiber 31.

The operation of the laser-scanning examination apparatus 30 according to this embodiment, having such a configuration, will be described below.

First, a case in which near-infrared ultrashort-pulse laser light is emitted from a first laser light source 11 will be described.

The ultrashort-pulse laser light that is allowed to pass through the multimode fiber constituting the first optical fiber 31 propagates in multiple transmission modes. These transmission modes are represented schematically in FIGS. 5A to 5C. FIGS. 5A to 5C show the intensity distribution of the ultrashort-pulse laser light at the light-emitting end of the first optical fiber 31. The hatched portions in the figures are regions where the light intensity is zero. More specifically, as shown in FIG. 5A, when ultrashort-pulse laser light of the lowest order transmission mode (that is, the $LP_{01}$ mode) propagates, there is no region in the core where the light intensity distribution is zero. On the other hand, for other transmission modes ($LP_{nm}$ modes, where $n \geq 1$ and $m \geq 1$), there are regions near the center of the core where the light intensity is zero, as shown in FIGS. 5B and 5C.

Therefore, like the laser-scanning examination apparatus 30 according to this embodiment, by positioning the pinhole member 33 at the intermediate image position of the focusing lens 32 which forms an image of the light-emitting surface of the first optical fiber 31, which is formed of a multimode fiber, among the ultrashort-pulse laser light of the multiple transmission modes propagating in the first optical fiber 31, only the ultrashort-pulse laser light of the lowest-order mode is selectively transmitted, and therefore, it is possible to block the passage of laser light of other transmission modes. By doing so, it is possible to prevent the pulse width of the ultrashort-pulse laser light from increasing, as in the case of propagation in a single-mode fiber. Thus, the specimen A can be irradiated with ultrashort-pulse laser light, with various short pulse widths, emitted by the first laser light source 11, and it is therefore possible to efficiently produce the multiphoton-excitation effect. In such a case, the fluorescence produced by the specimen A is reflected at the dichroic mirror 22, as in the first embodiment, is guided in the second optical fiber 6 (multimode fiber or fiber bundle), and is detected by the first optical detector 13.

Next, a description shall be given of the case where continuous-wave laser light is generated by a second laser light source 12.

Unlike the first embodiment, since the first optical fiber 31 is formed of a multimode fiber, the light-emitting surface thereof does not function as a confocal pinhole. However, in this embodiment, the focusing lens 32 is disposed opposite the light-emitting surface and the pinhole member 33 is disposed close to the image plane of the focusing lens 32. Therefore, this pinhole member 33 functions as a confocal pinhole, and it is thus possible for only the light produced at the image position of the objective lens 2 to return inside the first optical fiber 31.

Therefore, in the laser-scanning examination apparatus 30 according to this embodiment, a multiphoton-excitation effect can also be efficiently produced by the near-infrared ultrashort-pulse laser light emitted by the first laser light source 11, which allows efficient detection of the fluorescence obtained thereby. In addition, it is also possible to carry out confocal observation using the continuous-wave laser light emitted by the second laser light source 12.

The pinhole member 33 may have a variable inner diameter. Making the inner diameter variable, allows the confocal effect (the resolution in the optical-axis direction) to be adjusted. Doing so allows the ease of use to be improved; in contrast, there is some difficulty when providing the pinhole effect using the tip of the first optical fiber 5 on which the fluorescence is incident due to the confocal effect being fixed.

The light blocking part of the pinhole member 33 is formed of, for example, a metal plate that completely blocks the laser light and the fluorescence. Instead of this, however, it may be formed, for example, of an interference film that blocks ultrashort-pulse laser light with a wavelength of about 976 nm emitted by the first laser light source 11, continuous-wave laser light with a wavelength of 488 nm emitted by the second laser light source 12, and fluorescence produced by the specimen A in response to the continuous-wave laser light from the second laser light source 12, and that transmits fluorescence produced by the specimen A in response to the ultrashort-pulse laser light emitted by the first laser light source 11. In such a case, the dichroic mirror 22, the coupling lens 23, the optical fiber 6, the collimator lens 18, the barrier filter 19, and the first optical detector 13 become unnecessary.

As a result, with the ultrashort-pulse laser light having a wavelength of 976 nm, only the lowest-order mode is selectively transmitted by the pinhole member 33, in the same way as in the above, and therefore, a multiphoton-excitation effect is efficiently produced in the specimen A. On the other hand, the fluorescence produced in the specimen A reaches the pinhole member 33 via the objective lens 2, the imaging lens 10, the pupil-projection lens 9, the laser scanning unit 8, and the collimator lens 7 and passes through the light blocking part of the pinhole 33. As a result, the fluorescence is guided to the first optical fiber 31 (the multimode fiber) by the focusing lens 32 without experiencing the pinhole effect.

Then the fluorescence transmitted through the first optical fiber 31 passes through the coupling lens 17 and the dichroic mirror 16 and is detected by the second optical detector 14. Naturally, the dichroic mirror 16 is designed to have a wavelength characteristic that transmits the fluorescence. Since the fluorescence does not experience the pinhole effect imparted by the pinhole member 33, it is efficiently guided to the first optical fiber 31 without being blocked by the pinhole member 33.

In contrast, the continuous-wave laser light having a wavelength of about 488 nm and the associated fluorescence can be made to experience the confocal effect due to their being spatially restricted by the pinhole member 33.

Therefore, since a single first optical fiber 31 is sufficient to serve as the optical fiber for connecting the measurement head 3 and the optical unit 4, an advantage is afforded in that the measurement head 3 can be easily manipulated.

Next, a laser-scanning examination apparatus 40 according to a third embodiment of the present invention will be described with reference to FIGS. 6 and 7.

In the description of this embodiment, parts having the same configuration as those in the laser-scanning examination apparatus according to the first embodiment shown in FIG. 1 are assigned the same reference numerals, and a description thereof shall thus be omitted.

Figure 6:
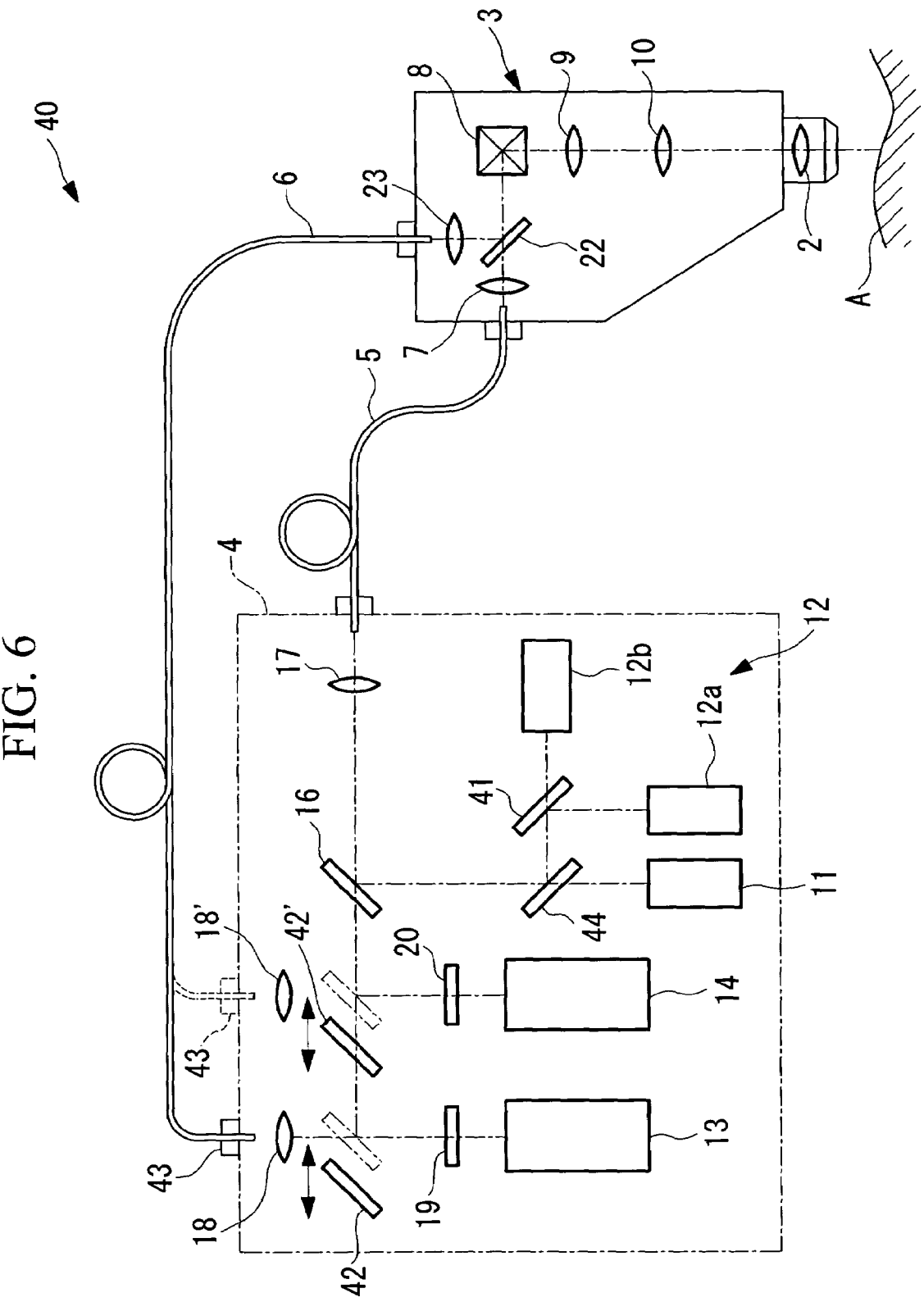
FIG. 6 is a schematic diagram showing the overall configuration of a laser-scanning examination apparatus according to a third embodiment of the present invention.

As shown in FIG. 6, in the laser-scanning examination apparatus 40 according to this embodiment, a second light source 12 that produces continuous-wave laser light includes two laser light sources 12a and 12b, whose optical axes are combined by a dichroic mirror 41. These laser light sources 12a and 12b have different wavelengths and they are alternately switched or used simultaneously when examining the specimen A, which is stained with two different dyes. Also, removable dichroic mirrors 42 and 42' are disposed between a first optical detector 13 and a collimator lens 18 and between a second optical detector 14 and a collimator lens 18', respectively. A second optical fiber 6 is removably attached by means of a connector 43 so as to be selectively positioned opposite either the first optical detector 13 or the second optical detector 14.

When carrying out examination of the specimen A using the multiphoton-excitation effect with the laser-scanning examination apparatus 40 according to this embodiment, first, it is selected whether to use the first optical detector 13 or the second optical detector 14 as the optical detector, depending on the wavelength of the fluorescence produced in the specimen A. For example, as shown by the solid lines in FIG. 6, when the first optical detector 13 is selected, the dichroic mirror 42 is withdrawn from between the first optical detector 13 and the collimator lens 18, and the connector 43 of the second optical fiber 6 is connected so that the fluorescence transmitted through the second optical fiber 6 is made incident on the first optical detector 13 via the collimator lens 18. Also, as shown by the dashed lines in FIG. 6, when the second optical detector 14 is selected, the connector 43 of the second optical fiber 6 is connected at a position opposite the second optical detector 14, and the dichroic mirror 42' is withdrawn, as shown by the solid lines. Accordingly, it is possible to selectively detect the fluorescence at either of the optical detectors 13 and 14, which have barrier filters 19 and 20, respectively, that are best suited for the wavelength of the fluorescence.

In this state, when near-infrared ultrashort-pulse laser light is emitted from the first light source 11, it is introduced to the first optical fiber 5 via dichroic mirrors 44 and 16 and a coupling lens 17. The ultrashort-pulsed laser light, which enters the measurement head 3 after being transmitted through the first optical fiber 5, then passes through a collimator lens 7, a dichroic mirror 22, a laser scanning unit 8, a pupil-projection lens 9, an imaging lens 10, and an objective lens 2 to irradiate the specimen A, and fluorescence is produced due to a multiphoton-excitation effect. The fluorescence produced returns along the same optical path, but is reflected at the dichroic mirror, passes through a coupling lens 23, and returns to the optical unit 4 via the second optical fiber 6. In the optical unit 4, the fluorescence transmitted through the second optical fiber 6 is detected by either the first optical detector 13 or the second optical detector 14 that is positioned opposite the second optical fiber 6.

Figure 7:
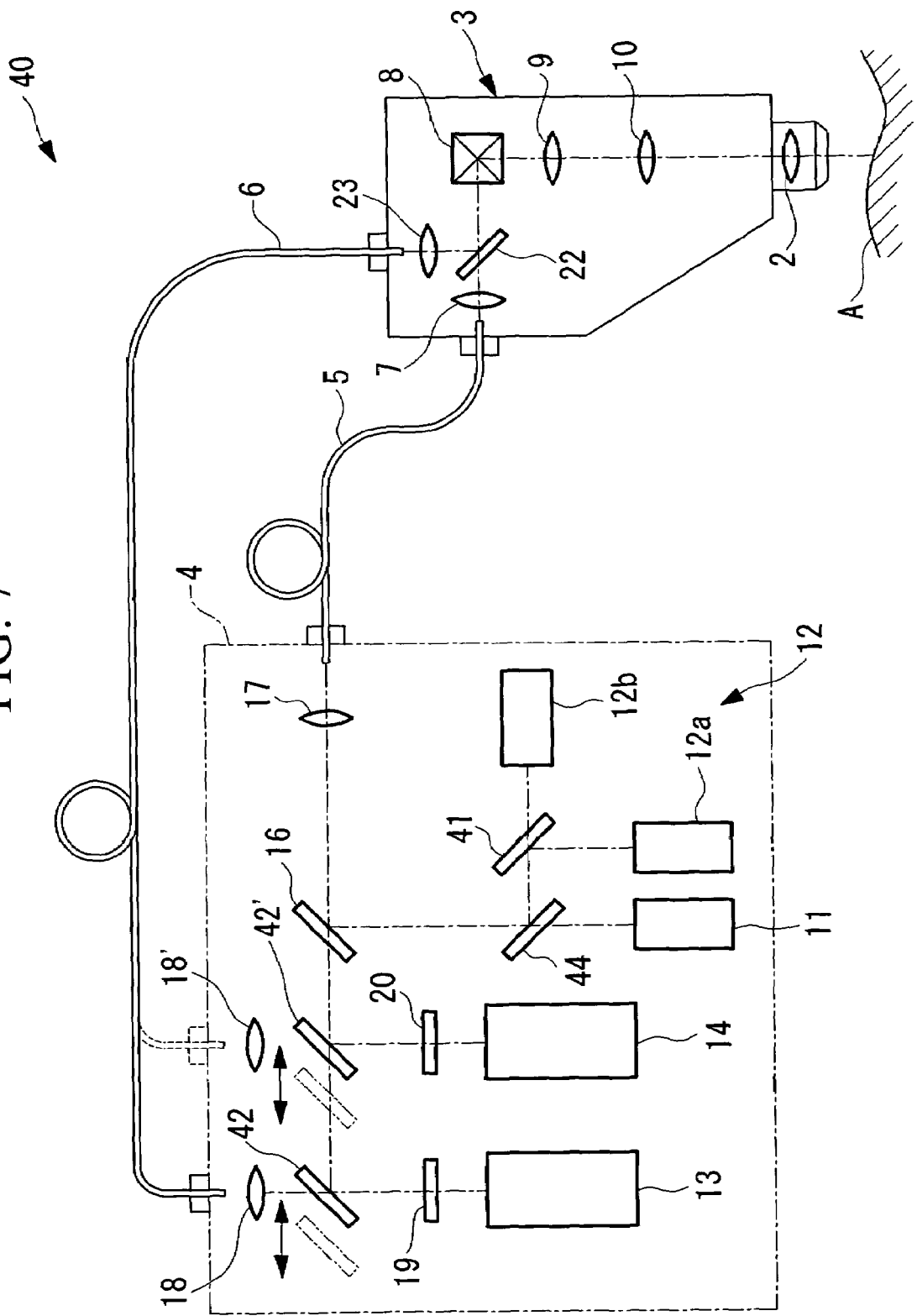
FIG. 7 is a schematic diagram showing the configuration of the laser-scanning examination apparatus in FIG. 6 when using continuous-wave laser light for examination.

When carrying out confocal examination with the laser-scanning examination apparatus 40 according to this embodiment, as shown in FIG. 7, the dichroic mirrors 42 and 42' are positioned so as to be inserted between the first optical detector 13 and the collimator lens 18 and between the second optical detector 14 and the collimator lens 18', respectively. Then, laser light of the respective wavelengths is simultaneously radiated from the two laser light sources 12a and 12b constituting the second light source 12. The laser light passes through the dichroic mirrors 41, 44, and 16, the coupling lens 17, and the first optical fiber 5 to enter the measurement head 3, where it passes through the collimator lens 7, the dichroic mirror 22, the laser scanning unit 8, the pupil-projection lens 9, the imaging lens 10, and the objective lens 2 to irradiate the specimen A. Fluorescence of two wavelengths produced in the specimen A returns along the same path to the optical unit 4, passes through the coupling lens 17, the dichroic mirrors 16, 42, and 42', and is detected by the optical detectors 13 and 14 having the barrier filters 19 and 20 that are best suited to the respective wavelengths of the fluorescence.

In this way, with the laser-scanning examination apparatus 40 according to the present invention, it is possible, by switching between common optical detectors, to carry out examination employing the multiphoton-excitation effect with the near-infrared ultrashort-pulse laser light emitted by the first light source 11 and confocal observation with the continuous-wave laser light of two wavelengths emitted by the second light source 12.

Depending on the wavelength characteristics, the second optical fiber 6 may be attached to the connector 43 while the dichroic mirrors 42 and 42' are inserted in the optical path to observe the fluorescence due to the multiphoton-excitation effect. Also, in order to more efficiently reflect the fluorescence from the first optical fiber 5, it is also possible for mirrors to be selectively switched, instead of the dichroic mirrors 42 and 42'.

Figure 8:
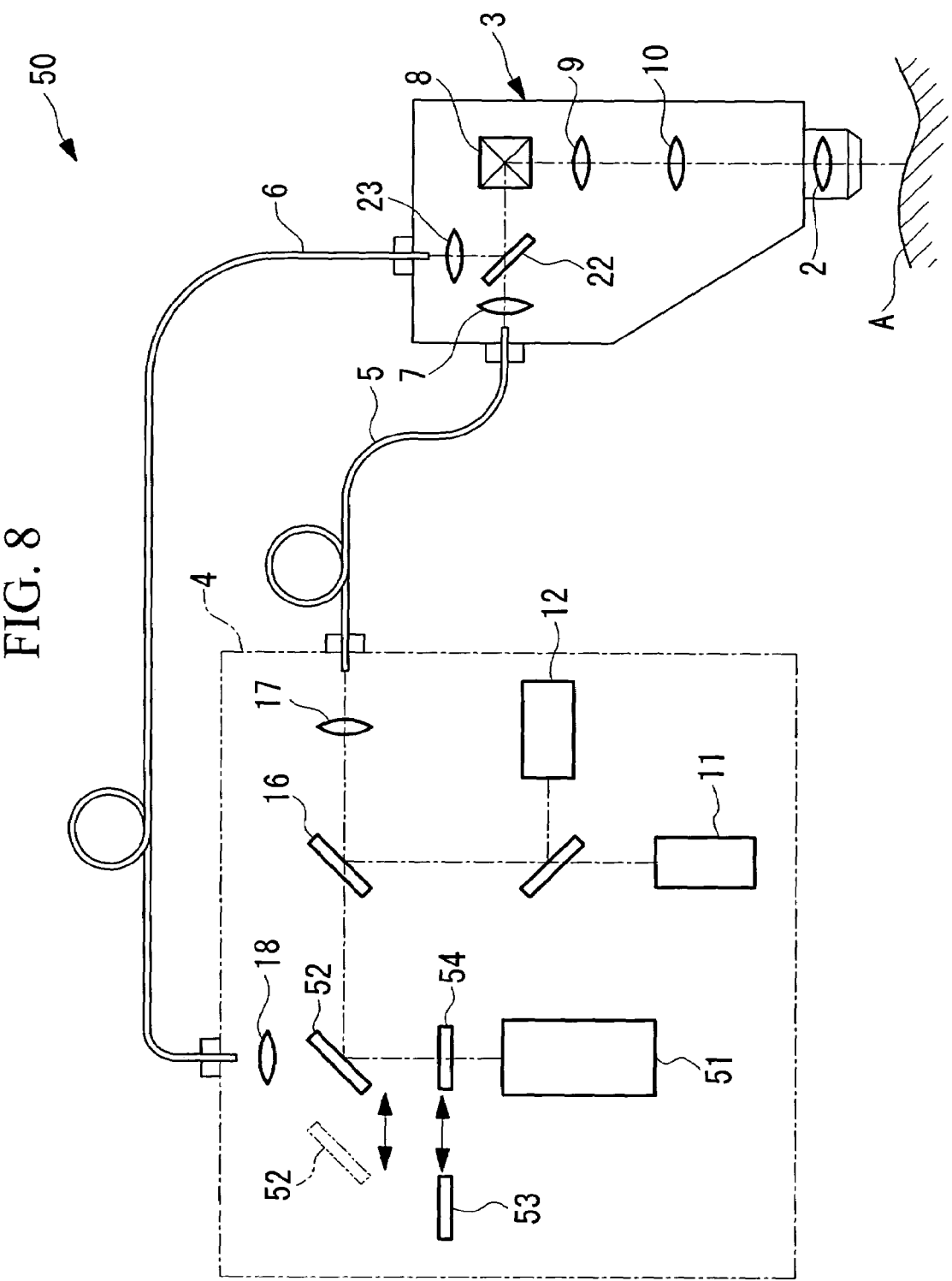
FIG. 8 is a schematic diagram showing the overall configuration of a laser-scanning examination apparatus according to a fourth embodiment of the present invention.

Next, a laser-scanning examination apparatus 50 according to a fourth embodiment of the present invention will be described with reference to FIG. 8.

In the description of this embodiment, parts having the same configuration as those in the laser-scanning examination apparatus 1 according to the first embodiment shown in FIG. 1 are assigned the same reference numerals, and a description thereof shall thus be omitted.

The laser-scanning examination apparatus 50 according to this embodiment includes a single optical detector 51, and a removable mirror 52 and replaceable barrier filters 53 and 54 are disposed between the optical detector 51 and a collimator lens 18. When near-infrared ultrashort-pulse laser light is emitted from a first light source 11, the mirror 52 is retracted to a position shown by the dotted lines, and the barrier filter 53, which allows only fluorescence having a wavelength produced by the multiphoton-excitation effect to pass therethrough, is inserted. On the other hand, when continuous-wave laser light is emitted from the second light source 12, the mirror 52 is inserted to a position shown by the solid lines, and the barrier filter 54, which allows fluorescence of a wavelength produced by irradiation with the continuous-wave laser light, is inserted With such a configuration, the optical detector 51 can be shared, which affords an advantage in that the number of components can be reduced, which lowers costs and allows the configuration of the system to be made more compact.

Next, a laser-scanning examination apparatus 60 according to a fifth embodiment of the present invention will be described with reference to FIGS. 9 and 10.

Figure 9:
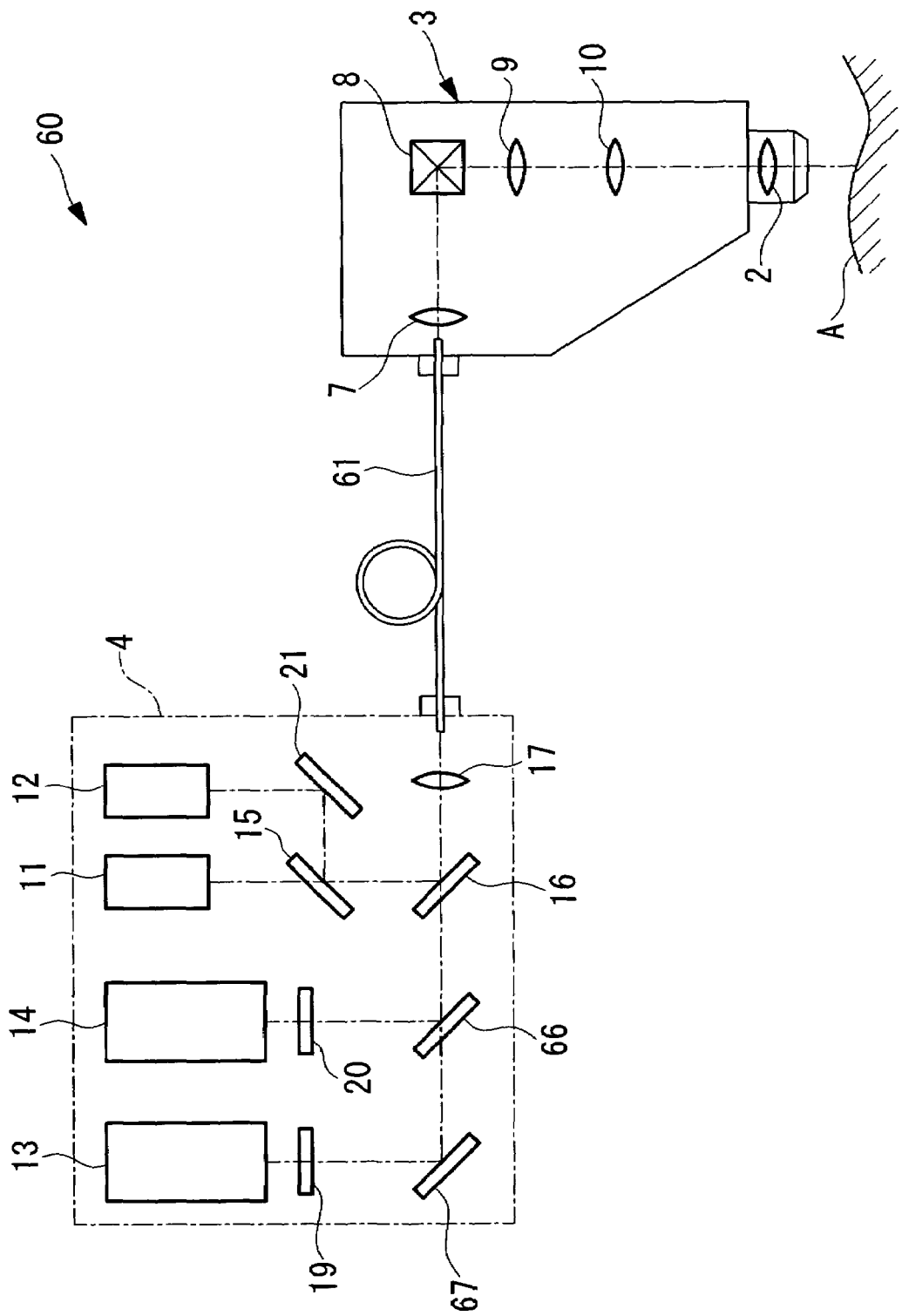
FIG. 9 is a schematic diagram showing the overall configuration of a laser-scanning examination apparatus according to a fifth embodiment of the present invention.

As shown in FIG. 9, the laser-scanning examination apparatus 60 according to this embodiment differs from the laser-scanning examination apparatuses 1, 30, and 40 according to the embodiments described above in that an optical unit 4 and a measurement head 3 are connected by a single optical fiber 61.

Figure 10:
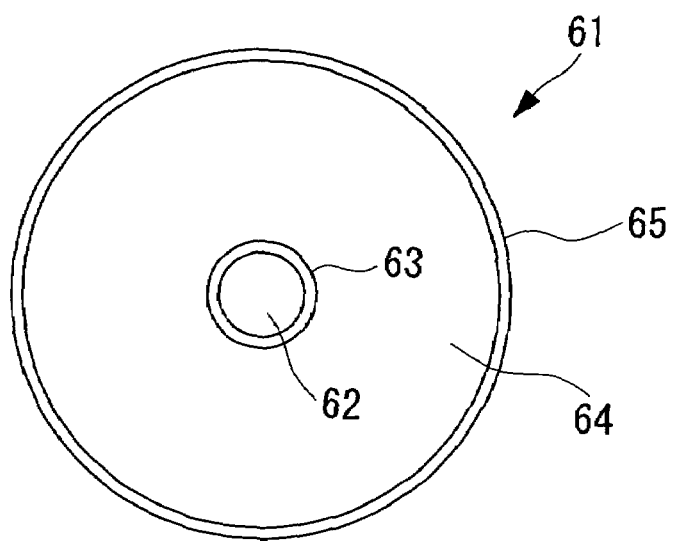
FIG. 10 is a cross-section showing the structure of an optical fiber in the laser-scanning examination apparatus in FIG. 9.

As shown in FIG. 10, the optical fiber 61 has a double configuration in which a first core 62 having a diameter equal to a single-mode fiber is disposed at the center, a second core 64 is disposed so as to encircle the first core 62 while being separated therefrom by a first cladding 63 which is disposed around it, and a second cladding 65 is further disposed around the second core 64.

The laser light from the first and second light sources 11 and 12 is made incident on the first core 62 at the center via dichroic mirrors 15, 21, and 16 and a coupling lens 17, and is transmitted therethrough. Thereafter, the laser light is irradiated onto a specimen A by means of the measurement head 3. Fluorescence produced in the specimen A is introduced into and transmitted through the first core 62 or the second core 64 by the collimator lens 7 in the measurement head 3, and is detected by first and second optical detectors 13 and 14 via the coupling lens 17, dichroic mirrors 16, 66, and 67, and barrier filters 19 and 20 in the optical unit 4.

With the laser-scanning examination apparatus 60 according to this embodiment, having such a configuration, when the laser light from the first and second light sources 11 and 12 is incident, by causing the laser light to pass through the first core 62, which has a narrow core diameter, it is possible to prevent the pulse width of the ultrashort-pulse laser light from increasing. As a result, the multiphoton-excitation effect can be efficiently generated.

Furthermore, with respect to the fluorescence returning from the measurement head 3, by returning the fluorescence produced by the ultrashort-pulse laser light from the first light source via the second core 64, which has a large core diameter, it is possible to reduce the amount of light loss, which allows bright fluorescence images to be acquired. In addition, by returning the fluorescence produced by the continuous-wave laser light from the second light source 12 via the first core 62, which has a small core diameter, it is possible to produce a confocal effect.

In the laser-scanning examination apparatus 60 according to this embodiment, since there is only a single optical fiber 61 joining the optical unit 4 and the measurement head 3, an advantage is afforded in that it is possible to increase the number of possible degrees of freedom in adjusting the position and orientation of the measurement head 3.

Figure 11:
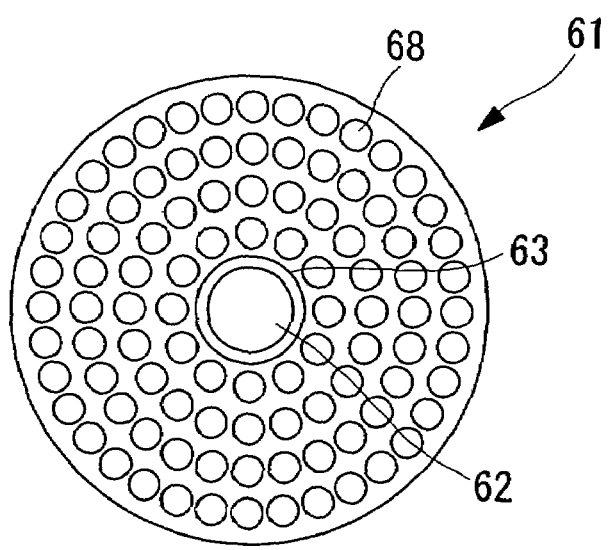
FIG. 11 is a cross-section showing a modification of the optical fiber in FIG. 10.

In this embodiment, the double-configuration optical fiber 61 shown in FIG. 10 has been given as an example of the optical fiber 61. Instead of this, however, as shown in FIG. 11, a fiber bundle in which a plurality of second cores 68 are disposed in a bundle around a first core 62 at the center may be employed. With this configuration too, the same advantages as those described above can be achieved, and making the optical fiber 61 more flexible allows the ease-of-handling to be improved.

What is claimed is:

1. A laser-scanning examination apparatus comprising:
   a first laser light source for producing ultrashort-pulse laser light;
   a second laser light source for producing continuous-wave laser light;
   a measurement head including an optical scanning unit for scanning the laser light from the first and second laser light sources on a specimen and an objective optical system for imaging the laser light scanned by the optical scanning unit onto the specimen;
   a first imaging unit for detecting return light from the specimen in response to the ultrashort-pulse laser light from the first laser light source;
   a second imaging unit for detecting return light from the specimen in response to the continuous-wave laser light from the second laser light source;
   a first optical fiber for connecting the first laser light source, the second laser light source, and the second imaging unit with the measurement head, the first optical fiber being configured to transmit the ultrashort-pulse laser light and the continuous-wave laser light to the measurement head and to transmit the return light from the specimen in response to the continuous-wave laser light to the second imaging unit; and
   a second optical fiber, having a core diameter larger than the first optical fiber, for connecting the first imaging unit with the measurement head, the second optical fiber being configured to transmit the return light from the specimen in response to the ultrashort-pulse laser to the first imaging unit.

2. A laser-scanning examination apparatus according to claim 1, wherein the first optical fiber is disposed at the center of the second optical fiber.

3. A laser-scanning examination apparatus according to claim 1, further comprising:
   a light-path switching mechanism,
   wherein the first imaging unit and the second imaging unit are constituted of the same imaging unit, and
   the light-path switching mechanism switches between a light path linking the first optical fiber and the imaging unit and a light path linking the second optical fiber and the imaging unit.

4. A laser-scanning examination apparatus comprising:
   a first laser light source for producing ultrashort-pulse laser light;
   a second laser light source for producing continuous-wave laser light;
   a measurement head including an optical scanning unit for scanning the laser light from the first and second laser light sources on a specimen and an objective optical system for imaging laser light scanned by the optical scanning unit onto the specimen;
   a first imaging unit for detecting return light from the specimen in response to the ultrashort-pulse laser light from the first laser light source;
   a second imaging unit for detecting return light from the specimen in response to the continuous-wave laser light from the second laser light source;
   a first optical fiber for connecting the first laser light source and the measurement head, the first optical fiber being configured to transmit the ultrashort-pulse laser light to the measurement head;
   a second optical fiber for connecting the second laser light source and the second imaging unit with the measurement head, the second optical fiber being configured to transmit the continuous-wave laser light to measurement head and to transmit the return light from the specimen in response to the continuous-wave laser light to the second imaging unit; and a third optical fiber, having a core diameter larger than the first and second optical fibers, for connecting the first imaging unit and the measurement head, the third optical fiber being configured to transmit the return light from the specimen in response to the ultrashort-pulse laser light to the first imaging unit.

5. A laser-scanning examination apparatus according to claim 4, wherein the first optical fiber and the second optical fiber are formed of single-mode fibers or photonic crystal fibers; and a cutoff wavelength of the second optical fiber is set to be smaller than a cutoff wavelength of the first optical fiber.

6. A laser-scanning examination apparatus comprising:

a first laser light source for producing ultrashort-pulse laser light;

a second laser light source for producing continuous-wave laser light;

a measurement head including an optical scanning unit for scanning the laser light from the first and second laser light sources on a specimen and an objective optical system for imaging the laser light scanned by the optical scanning unit onto the specimen;

a first imaging unit for detecting return light from the specimen in response to the ultrashort-pulse laser light from the first laser light source;

a second imaging unit for detecting return light from the specimen in response to the continuous-wave laser light from the second laser light source;

a first optical fiber, wherein the first optical fiber is a multimode fiber for connecting the first laser light source, the second laser light source, and the second imaging unit with the measurement head, the first optical fiber being configured to transmit the ultrashort-pulse laser light and the continuous-wave laser light to the measurement head and to transmit the return light from the specimen in response to the continuous-wave laser light to the second imaging unit; and a second optical fiber, wherein the second optical fiber is one of a multimode fiber and a fiber bundle for connecting the first imaging unit and the measurement head, the second optical fiber being configured to transmit the return light from the specimen in response to the ultrashort-pulse laser to the first imaging unit;

wherein the measurement head includes a focusing lens that forms an intermediate image of the laser light coming from the first and second laser light sources and transmitted by the first optical fiber, and a pinhole member, disposed close to the position of the intermediate image, that admits passage of only the vicinity of the center of the intermediate image.

7. A laser-scanning examination apparatus according to claim 6, wherein the diameter of an opening in the pinhole member is variable.

8. A laser-scanning examination apparatus comprising:

a first laser light source for producing ultrashort-pulse laser light;

a second laser light source for producing continuous-wave laser light;

a measurement head including an optical scanning unit for scanning the laser light from the first and second laser light sources on a specimen and an objective optical system for imaging the laser light scanned by the optical scanning unit onto the specimen;

an imaging unit for detecting return light from the specimen in response to the laser light from the first and second laser light sources; and a multimode fiber for connecting the first laser light source, the second laser light source, and the imaging unit with the measurement head, wherein the measurement head includes a focusing lens that forms an intermediate image of the laser light coming from the first and second laser light sources and transmitted by the multimode fiber, and a pinhole member, provided in near the position of the intermediate image, that admits passage of only the vicinity of the center of the intermediate image, and the pinhole member is formed of a material that blocks the ultrashort-pulse laser light, the continuous-wave laser light, and return light from the specimen in response to the continuous-wave laser light and that allows passage of the return light from the specimen in response to the ultrashort-pulse laser light.

9. A laser-scanning examination apparatus comprising:

a first laser light source for producing ultrashort-pulse laser light;

a second laser light source for producing continuous-wave laser light;

a measurement head including an optical scanning unit for scanning the laser light from the first and second laser light sources on a specimen and an objective optical system for imaging the laser light scanned by the optical scanning unit onto the specimen;

an imaging unit for detecting return light from the specimen in response to the laser light from the first and second laser light sources; and an optical fiber having a first core and second core, wherein the second core is disposed so as to encircle the first core, the first core being adapted to transmit the ultrashort-pulse laser light and the continuous-wave laser light to the measurement head and to transmit the return light from the specimen in response to the continuous-wave laser light to the imaging unit, and wherein the first core and the second core are configured to transmit the return light from the specimen in response to the ultrashort-pulse laser to the imaging unit.

* * * * *